United States Patent [19]
Faraci et al.

[11] Patent Number: 5,847,155
[45] Date of Patent: Dec. 8, 1998

[54] AROMATIC PYRROLIDINE AMIDE PROLYL ENDOPEPTIDASE INHIBITORS

[75] Inventors: W. Stephen Faraci, East Lyme; Arthur A. Nagel, Gales Ferry; Robin W. Spencer, East Lyme; Fredric J. Vinick, Waterford, all of Conn.

[73] Assignee: Pfizer Inc, New York, N.Y.

[21] Appl. No.: 592,221

[22] Filed: Jan. 26, 1996

Related U.S. Application Data

[63] Continuation of Ser. No. 960,374, filed as PCT/US91/03390, May 15, 1991, abandoned, which is a continuation of Ser. No. 532,534, Jun. 4, 1990, abandoned.

[51] Int. Cl.$^6$ ..................... C07D 209/14; C07D 405/02; A01N 43/36; A01N 43/38
[52] U.S. Cl. ................ 548/400; 514/408; 514/418; 514/422; 514/423; 548/400; 548/467; 548/468; 548/469; 548/492; 548/518; 548/525
[58] Field of Search .......................... 544/53; 546/244; 548/400, 517, 525, 465, 467, 468, 469, 492, 518; 514/422, 423, 408, 415, 419

[56] References Cited

U.S. PATENT DOCUMENTS

| | | | |
|---|---|---|---|
| 4,208,205 | 6/1980 | Fawzi | 71/118 |
| 4,610,991 | 9/1986 | Bailey | 514/318 |
| 4,857,537 | 8/1989 | Toda et al. | 514/365 |
| 4,956,380 | 9/1990 | Toda et al. | 514/422 |
| 4,977,180 | 12/1990 | Toda et al. | 514/423 |

FOREIGN PATENT DOCUMENTS

| | | |
|---|---|---|
| 098951A2 | 1/1983 | European Pat. Off. . |
| 222371A2 | 5/1987 | European Pat. Off. . |
| 268190A1 | 5/1988 | European Pat. Off. . |
| 277588A1 | 8/1988 | European Pat. Off. . |
| 345428A1 | 4/1989 | European Pat. Off. . |
| 280956B1 | 10/1992 | European Pat. Off. . |

OTHER PUBLICATIONS

Chemical Abstracts, 46983s (Dupont), 94, 544.
Chemical Abstracts, 74803k (Kyowa), 84, 433.
Chemical Abstracts, 99709a (Indian J. Chem), 74, 481.

*Primary Examiner*—Shean C. Wu
*Attorney, Agent, or Firm*—Peter C. Richardson; Paul H. Ginsburg; Raymond M. Speer

[57] ABSTRACT

A series of aromatic pyrrolidine derivatives and suitable pharmaceutically acceptable salts thereof are disclosed. These compounds are useful as PEP inhibitors in the treatment of Alzheimer's disease, amnesia, dementia, anxiety ischemia, or stroke.

1 Claim, No Drawings

AROMATIC PYRROLIDINE AMIDE PROLYL ENDOPEPTIDASE INHIBITORS

This is a continuation of application Ser. No. 07/960,374, filed on Jan. 27, 1993, now abandoned, which was the National Phase application of PCT application serial number PCT/US91/03390, which was a continuation of U.S. patent application Ser. No. 07/532,534, filed Jun. 4, 1990, now abandoned.

BACKGROUND OF THE INVENTION

The present invention relates to aromatic pyrrolidine and thiazolidine amides, to pharmaceutical compositions comprising such compounds, to methods of preparing such compounds, and to the use of such compounds for enhancing learning behavior and memory and in the treatment of Alzheimer's disease and in prevention of ischemic damage following a stroke or other injury to the central nervous system.

The foregoing compounds are prolyl endopeptidase (PEP) inhibitors. Prolyl endopeptidase is a cytosolic serine protease that hydrolyzes polypeptides after the amino acid proline in the peptide sequence. This enzyme is also known to cut (in vitro) LHRH, vasopressin, neurotensin, oxytocin, substance P and bradykinin. PEP has been found to be inhibited by Z-prolyl-prolinal as well as other compounds, some of which are believed to have an anti-amnesia effect. (W. Frogtl, et al., *Pharmacopsychiat.*, 22 54–100 (Supplement) (1989); S. Wilk, et al., *J. Neurochem*, 4 (1983), 69–75; N. Katsube, et al., *Japan J. Pharmacol.* 49 (1989)). Some substituted pyrolidine compounds are also believed to be PEP inhibitors (See, European Patent Nos. 88-294328 and 88-294329).

As stated above PEP hydrolyzes proline-containing peptides having biological activity, one of which is vasopressin, a peptide which is believed to be involved with memory processes in the brain. Since compounds that inhibit PEP have been found to have some anti-amnesic effects, it is believed that these inhibitors, as a result of blocking the activity of PEP, have the effect of leading to an increase in the concentration of vasopressin or its metabolites in the brain (T. Yoshimoto, et al., *J. Pharmacobio-Dyn.*, 10, 730–735 (1987); J. P. H. Burbach, et al, *Science*, 221, 1310–1312 (1983)).

SUMMARY OF THE INVENTION

The present invention relates to compounds of the formula

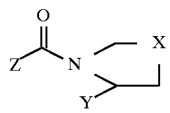

wherein X is S or $(CH_2)_n$ wherein n is 1 or 2; Y is —CHO, —COCF$_3$, C$_1$ to C$_6$ hydroxyalkyl, —COCO$_2$R, or hydrogen; and Z is

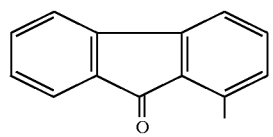

-continued

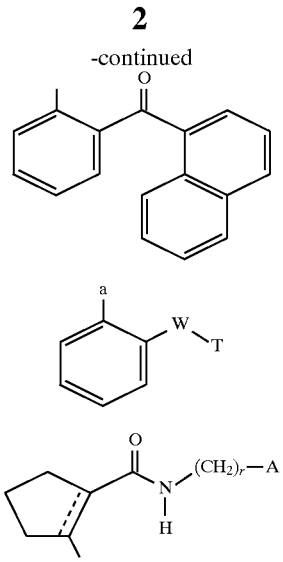

wherein W is

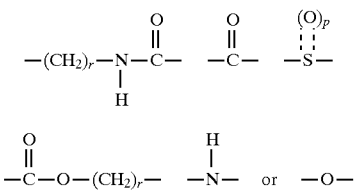

wherein T is

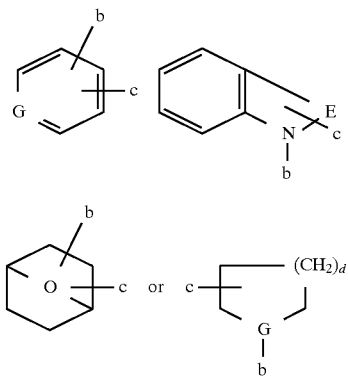

wherein each broken line represents an optional double bond, p is 0 or 2, A is phenyl or C$_3$ to C$_6$ cycloalkyl, G is CH or N, E is a C$_2$ to C$_3$ alkyl or alkylene group, d is 1 to 2; and r is 1 to 5 with the proviso that the bond of Z to formula (I) is at position a or b and the bond of T with W is at position c and if at b and b and c are each floating bonds, c is positioned at the ring substituent adjacent to the substituent at position b and pharmaceutically acceptable salts thereof. The preferred substituents for Z include the following:

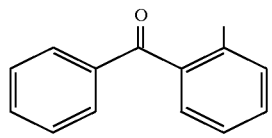

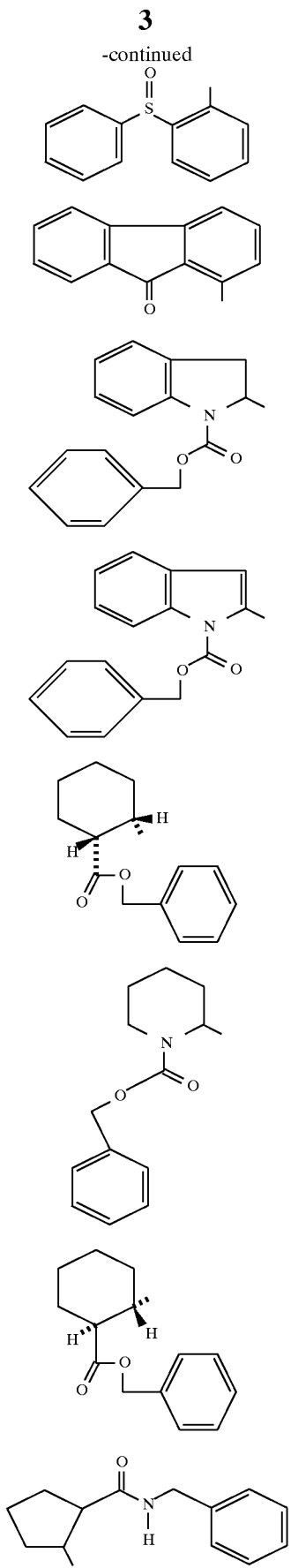
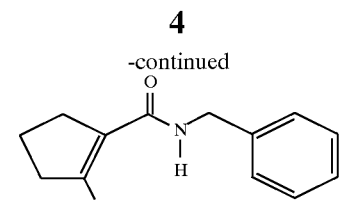

The present invention also relates to a pharmaceutical composition comprising an amount of a compound of the present invention effective in the treatment of Alzheimer's disease, amnesia, dementia, anxiety, ischemia, and stroke damage and a pharmaceutically acceptable carrier.

The present invention also relates to a method of treating a condition selected from Alzheimer's disease, amnesia, dementia, anxiety, ischomia or stroke comprising administering to a mammal in need of such treatment an amount of a compound of the present invention effective in treating such condition.

The following are preferred compounds of the present invention:

1-[2-(phenylsulfonyl)benzoyl]2-pyrrolidinecarboxaldehyde;

2-[2-formyl-1-pyrrolidinyl)carbonyl]-1H-indoie-1-carboxylic acid, phenylmethyl ester;

1-[9-oxo-9H-fluoren-1-yl)carbonyl]-2-pyrrolidinecarboxaldehyde;

1-(2-benzoylbenzoyl)-2-(trifluoroacetyl)pyrrolidine;

2-[(2-formyl-1-pyrrolidinyl)carbonyl]-1-piperidinecarboxylic acid, phenylmethyl ester;

2-[(2-formyl-1-pyrrolidinyl)carbonyl]-2,3-dihydro-1H-indole-1-carboxylic acid, phenylmethyl ester;

2-[(2-formyl-1-pyrrolidinyl)carbonyl]-cyclohexanecarboxylic acid, phenylmethyl ester;

2-[(2-formyl-1-pyrrolidinyl)carbonyl]-N-(phenylmethyl)cyclopentanecarboxamide; and 2-[(2-formyl-1-pyrrolidinyl)carbonyl]-cyclohexanecarboxylic acid, phenylmethyl ester.

Other specific compounds of the present invention include the following:

Cis-2-[(2-formyl-1-pyrrolidinyl)carbonyl]-cyclohexanecarboxylic acid, phenylmethyl ester;

2-[(4-formyl-3-thiazolidinyl)carbonyl]-2,3-dihydro-N-(phenylmethyl)-1H-Indole-1-carboxamide;

1-[[2-(1-oxo-3-phenylpropyl)-1-pyrrolidinyl]-carbonyl]-2-(trifluoroacetyl)-Pyrrolidine;

2-[(2-formyl-1-pyrrolidinyl)2,3-dihydro-1H-Indole-1-carboxylic acid, phenylmethyl ester;

Cis-2-[(4-formyl-3-thiazolidinyl)carbonyl]-cyclohexanecarboxylic acid, phenylmethyl ester;

(S) -2-[[2-(trifluoroacetyl)-1-pyrrolidinyl]carbonyl]-N-(phenylmethyl)-Benzamide;

(S) -N-[2-[[2-(trifluoroacetyl)-1-pyrrolidinyl]carbonyl)phenyl]-Benzamide;

2-[[2-(trifluoroacetyl)-1-pyrrolidinyl]carbonyl]-1H-Indole-1-carboxylic acid, phenylmethyl ester;

1-[2-(phenylthio)benzoyl]-2-Pyrrolidinecarboxaldehyde; and (S)-1-(2-phenoxybenzoyl)-2-Pyrrolidinecarboxaldehyde.

DETAILED DESCRIPTION OF THE INVENTION

The following reaction schemes illustrate the preparation of compounds of the present invention.

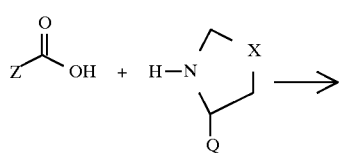

(1)     (2)

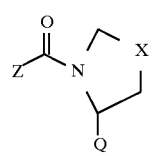

(3)

In the reaction scheme, Q can be hydrogen, a hydroxyalkyl group, or an alkyl ester group. An amide (3) is synthesized by a dehydration reaction through the use of a reagent capable of activating the acid (1). Such reagents include organic carbodiimides and anhydrides, such as dicyclohexyl carbodiimide and 1-ethyl-3-(3-dimethylaminopropyl) carbodiimide, preferably the latter. When the activated acid is in the presence of the pyrrolidine (2), the formation of the amide (3) proceeds. This reaction can be performed in an aprotic solvent such as methylene choride or tetrahydrofuran, preferably methylene chloride. Other reagents that promote the activation of the acid can be added to further facilitate the reaction, such as 1-hydroxy benzotriazole hydrate. The reaction is run at a temperature of between 25° C. and 30° C., preferably, ambient temperature. The reaction mixture is then washed with water and the organic phases evaporated to yield the amide (3).

When Q is a hydroxyalkyl group, that group can be oxidized to form the corresponding aldehyde. The oxidation is carried out in an aprotic solvent, preferably a halogenic aprotic solvent such as methylene chloride. An oxidizing reagent such as dimethyl sulfoxide (DMSO) is then used to convert the hydroxy group to the carbonyl group. The DMSO is activated using reagents such as trifluoroacetic anhydride, trifluoroacetic acid, or oxalyl chloride, preferably trifluoroacetic anhydride. The reaction solution is then quenched with water and dried to yield product.

Where Q is an alkylester group, the ester group of (3) can then be reacted in a Dakin-West reaction with trifluoroacetic acid and trifluoroacetic anhydride to convert the ester group to form the corresponding trifluoracetyl group.

Compounds of Formula I which are bases, such as those containing a pyridine substituent, are capable of forming acid addition salts with pharmaceutically acceptable acids. These acid addition salts may be prepared by reacting the base form of the appropriate compound of formula I with one or more equivalents, preferably with an excess, of the appropriate acid in an organic solvent, for example, diethyl ether or an ethanol/diethyl ether mixture. Suitable acids to form these salts include the common mineral acids, e.g. hydrohalic, sulfuric, or phosphoric acid; the organic acids, e.g. ascorbic, citric, lactic, aspartic or tartaric acid or their aqueous solutions whose pH has been adjusted to 5.5 or less; and acids which are sparingly soluble in body fluids and which impart slow-release properties to their respective salts, e.g. pamoic or tannic acid or carboxymethyl cellulose. The preferred salt is the hydrochloride salt.

The compounds of formula I and appropriate pharmaceutically acceptable salts thereof are useful in the treatment of CNS disorders including various memory of learning dysfunctions associated with diseases such as Alzheimer's disease. Other mental conditions such as amnesia, dementia, anxiety, ischemia, and damage caused by a stroke can also be treatable with the present invention. The compounds of this invention are, in general, less toxic and have a broader therapeutic window than known compounds such as tacrine and physostigmine, making them therapeutically preferred.

The dosage of the compounds of the present invention will vary with the form of administration and the particular compound chosen. Furthermore, it will vary with the particular subject as well as the age, weight and condition of the subject under treatment as well as with the nature and extent of the symptoms. Generally, however, a dose in the range of about 1 to about 300 mg/day, taken in single or divided doses will be administered.

Generally, treatment is initiated with small dosages substantially less than the optimum dose of the compound. Thereafter, the dosage is increased by small increments until the optimum effect under the circumstances is reached.

The compounds of the present invention are used alone or in combination with pharmaceutically acceptable carriers, the proportion of which is determined by the solubility and chemical nature of the compound, chosen route of administration, and standard medical practice. For example, they are administered orally in the form of capsules, tablets, suspensions or solutions or they may be injected parenterally. Capsules and tablets are the preferred mode of administration. For parenteral administration, they can be used in the form of a sterile solution containing other solutes, for example, enough saline or glucose to make the solution isotonic.

Capsule and tablet compositions may contain the active ingredient in admixture with one or more pharmaceutical excipients suitable for the manufacture of capsules and tablets. Suitable pharmaceutical excipients are, for example, starch, milk sugar, and certain types of clay. The tablets can be uncoated or they can be coated by known techniques so as to delay disintegration and absorption in the gastrointestinal tract and thereby provide a sustained action over a longer period.

Aqueous suspensions of the compounds of formula I contain the active ingredient in admixture with one or more pharmaceutical excipients suitable for the manufacture of aqueous suspensions. Suitable excipients are, for example, methylcellulose, sodium alginate, gum acacia, lecithin and so forth. Aqueous suspensions can also contain one or more preservatives, one or more coloring agents, one or more flavoring agents, and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

Assays

The following assays are used to evaluate the effectiveness of the compounds of the present invention.

I. In Vitro Enzyme Assay

A. Materials

Assay Buffer:

0.1M Tris[hydroxymethyl]aminomethane (Tris)

1.0 mM DL-dithiothreitol (DTT) (SIGMA D 0632)
Use acetic acid to adjust to pH 7.4; keep at 25° C.
Dilution Buffer:
0.01M Tris
2.0 mM Ethylenedramenetetroacetic acid (EDTA)
adjust to pH 8.3 at 25° C.
dilute 1:1 with glycerol for enzyme use
Substrate:
0.5 mM (N-carbobenzyloxy-glycyl-prolyl-(4-methyl-7-amino-coumarinamide)(Z-gly-pro-AMC) (BACHEM I1145) as a stock solution.
Dissolve in dimethylsulfoxide (DMSO)
bring to 40% v/v with assay buffer.
Enzyme:
The mouse brain prolylendopeptidase (mbPEP) is purified according to the method disclosed in Orlowski, M., et al., *J. Neurochemistry*, 33, 461–469 (1979). Once purified, the mbPEP is kept at 0° to 4° C. stored in a solution of 1:1/Dilution Buffer:glycerol.
Test Compound Solution:
Compounds to be assayed are dissolved in 100% DMSO to a concentration of 10 mM. The solution is then diluted with assay buffer to yield a test compound concentration of from 1 nanomolar to 1 micromolar depending upon the inhibitory potency of the compound, and a final concentration of DMSO of 0.2% or less.

B. Procedure

The reaction cuvette contains the following items (listed in order of addition):

1980 microliters assay buffer 10 microliters (0.5 mM) substrate 1 microliter of Test Compound Solution 10 microliters mbPEP (1:50 dilution with dilution buffer)
Fluorescence data is collected continuously with excitation at 380 nm and emission at 460 nm.

C. Data Interpretation

Each compound is tested to determine to what extent it is capable of inhibiting the activity of the enzyme mbPEP. The measure of potency ($K_i$) for each test compound is the concentration of that compound which reduced enzyme activity by 50% of the control value as shown by the fluorescence data. The control value is determined by running the assay using 0.2% DMSO. $K_i$ is determined by a non-linear least squares analysis of the steady state reaction rates, using, typically, between 1 nanomolar and 10 micromolar of test compound. For those compounds which exhibit slow, tight-binding behavior, both $K_i$ and $k_{on}$, the latter being the second-order rate constant of approach to the steady state, are determined.

II. Ex Vivo Enzyme Assay

Male CD-1 mice (20–40 gm) obtained from Charles River Laboratories, Cambridge, Mass. are used in the ex vivo and in vivo experiments. In the ex vivo assay, the control group of mice receive an intraperitoneal injection (0.25 ml) of a saline vehicle (5:5:90/DMSO: EMULPHOR (trademark of GAF Corp.): saline). The test compounds are administered by way of the saline vehicle. Each test compound is prepared for administration in the saline vehicle by first dissolving the compound in DMSO followed by addition of the saline and the EMULPHOR components of the solution.

The test group of mice each receive a single intraperitoneal injection of compound (0.25 ml) at 32 mg of compound per g weight of the mouse into which it is to be introduced. The control group of mice only receive the saline vehicle. A specific number of the mice in the test group are then decapitated at various time intervals thereafter (10–360 minutes). As quickly as possible after decapitation, the brain is removed, weighed, and homogenized (in a homogenizer fitted with a Teflon pestle) with an equal volume of ice-cold Tris buffer (0.1M Tris, 0.5 mM EDTA, at pH 8.3). Immediately, 1 microliter of the homogenate is added to an assay cuvette containing 2.0 mL of a second buffer (0.1M Tris, 0.1M NaCl, 1 mM DTT; pH 7.4) and 1.25 $\mu$M of substrate (Z-gly-pro-AMC). The rate of PEP enzyme activity is measured fluorometrically (380 nm excitiation, 460 nm emission) at 25° C. The mice in the control group are decapitated at one time and the same procedure is followed to determine the enzyme rate for them. The enzyme rate at each time interval from the animals in the test group are compared with the enzyme rate of the control group and reported as percent inhibition.

III. In Vivo Behavioral Assay

The in vivo testing involves measuring passive avoidance in mice using a shuttle box. The shuttle box which can be used is the model E13-08 manufactured by the Colbourn Instruments, Lehigh Valley, Pa. The time measurements to be assimilated during the tests can be retrieved by LAB LINE R (trademark) equipment from State Systems Inc., Kalamazoo, Mich.

The shuttle box is used to test for antagonism of the amnesia brought on by the anticholinergic agent scopolamine. Scopolamine is a drug known to induce amnesia when administered to laboratory animals. Such tests have been used to predict the usefulness of drugs in the treatment of memory problems that accompany old age, in particular, Alzheimer's disease.

The mice to be tested are divided into four groups: Group I receives one injection of scopolamine and a second injection of the compound to be tested and is used to determine the antagonistic effect of the test compound on scopolamine amnesia. Group II receives one injection of scopolamine and a second injection of saline. Group III receives, one injection of the test compound and a second of saline. Group IV receives two injections of saline. The Group IV mice are the control in the experiment while the Group II and Group III are used to ascertain the individual effect of the scopolamine and the test compound, respectively, on the animals. For each group receiving scopolamine, these injections are given fifteen minutes before the training procedure.

A. Training Procedure

The mice in all four groups are allowed to acclimate to the animal facility in which they are housed for seven days. The mice are then administered the appropriate injections and subjected to a training procedure in the shuttle box.

Each mouse is placed in the first side at the shuttle box facing away from the door which opens into the second side which has the electrically charged floor. The mouse is allowed to pass through the door into the second side where it experiences an electric shock, at which time it returns to the first side, also through the door. The amount of time between when the mouse is placed in the first side and when it exits the second side to return to the first side is referred to as the training step-through latency (training STL).

During the training procedure, mice which do not cross over to the second side within one minute or do not escape the footshock of the second side within 20 seconds are discarded from the experiment. Between training and test procedures, the animals are housed 12 per cage and are not handled or disturbed. All behavioral manipulations are conducted between 7:00 AM and 3:00 PM.

B. Test Procedure

Twenty-four hours after the training procedure the four groups of mice are tested resulting in a test step-through latency (test STL) score. Both the training STL and test STL twenty-four hours later for the control group should be roughly the same. With regard to the test group, if the two STL scores are roughly the same, the test compound does not effectively antagonize the scopolamine. If, however, the test STL score is lower and approaches the STL scores of the control group, this is evidence that the test compound is a scopolamine antagonist and thus reverses the amnesia caused by the scopolamine.

Set forth below are preparations A, B, and C illustrating the preparation of starting materials for compounds of the present invention. Following the Preparations are Examples illustrating the preparation of compounds of the present invention. All melting points are uncorrected.

Preparation A 2-(Phenylthio)-benzoic Acid 5.6 g (0.10 mol) potassium hydroxide, 7 ml water, 30 ml benzene and 7.7 g (0.05 mol) thiosalicyclic acid were combined and heated at reflux under a Dean Stark trap. After the water had been collected, 50 ml of dimethylformamide was added and the mixture slowly heated to 140°–150° C. to remove the benzene. An additional 10 ml of dimethylformamide and 0.25 g (1.75 mmol) of cuprous oxide were then added. 5.8 ml (0.051 mol) of iodobenzene was slowly added over a period of 20 minutes while the temperature was maintained at 140°–150° C. The reaction mixture gradually became a solution and gentle reflux was continued for 18 hours. The mixture was then cooled and poured over ice. The pH was adjusted to 10.0 and precipitated solids removed by filtration. The filtrate was washed with two portions of ethyl acetate (the organics were discarded) and adjusted to pH 2.5 with 1N HCl. A precipitate formed which was collected by filtration and then recrystallized from aqueous isopropanol to yield 9.5 g (83%) of the title compound.

Preparation B 2-(Phenylsulfonyl)-benzoic Acid 5.0 g (0.022 mol) of the title compound of Preparation A, 13.3 ml (0.13 mol) of 30% aqueous hydrogen peroxide, and 75 ml glacial acetic acid were combined and the resulting solution heated at 80°–90° C. for 18 hours. The solution was diluted with 500 ml of water and extracted with five portions of methylene chloride. The combined organic extracts were washed with brine, dried, and evaporated to give an oil which crystallized upon addition of toluene. The resulting white solid was collected by filtration, washed with hexane and dried to yield 4.3 g (74%) of the title compound. $^1$H NMR (CDCl$_3$) δ: 8.22(m,1H); 7.60–7.80 (m,3H); 7.20–7.40 (m,3H).

Preparation C

4-Thiazolidinemethanol 9.1 g of 4-ethoxycarbonylthiazolidine hydrochloride was added to 500 ml of chloroform. 1.1 equivalents of triethylamine (7.6 ml, 0.055 mol) was added and the solvent then evaporated. The residue was triturated with ether (500 ml) and filtered. The filtrate was evaporated to yield the free base as an oil (7.2 g).

3.4 g (0.0–23 mol) of calcium chloride dihydrate was dissolved in 120 ml of ethanol and the solution cooled to −30° C. A solution of sodium borohydride in 200 ml of ethanol was then slowly added, keeping the temperature below −20° C. The mixture was stirred for 20 minutes at −20° C. or lower. A solution of the ester of the free base in 30 ml of ethanol was then added. The reaction was stirred for 5 hours at below −20° C., then slowly warmed to room temperature and allowed to stir for 18 hours. The mixture was cooled to 15° C. and acidified with ethanol saturated with HCl gas. Solvent was removed under reduced pressure and the residue dissolved in 1:1/water:methylene chloride. The pH was adjusted to 2.5 with ammonium hydroxide and the methylene chloride layer was separated from the water layer. The pH of the water layer was then adjusted to 9.5 with ammonium hydroxide. The aqueous phase was extracted with several portions of methylene chloride, and the combined organic extracts were evaporated to give a white tacky solid. The solid was recrystallized by dissolving it in methylene chloride and adding enough hexane to cause recrystallization and yield 1.6 g (27%) of the title compound.

EXAMPLE 1

3-(2-Benzoylbenzoyl)-4-thiazolidinemethanol 1.9 g (8.4 mmol) of o-benzoylbenzoic acid and 1.13 g (8.4 mmol) of 1-hydroxybenzotriazole hydrate were combined in 50 ml of methylene chloride and stirred for 20 minutes at room temperature. 1.0 g (8.4 mmol) of 4-thiazolidinemethanol was added, followed by 1.6 g (8.4 mmol) of ethyl-3-(3-dimethylaminopropyl)carbodiimide. The reaction mixture was stirred for 18 hours at room temperature and washed with water, first at pH 2.5 and then at pH 9.5. The organic phase was dried and evaporated to give a foam which was chromatographed on silica gel using 1:1/chloroform:ethyl acetate as the eluant to yield 1.1 g (40%) of the title compound. $^1$H NMR (CDCl$_3$) δ: 7.4–7.85 (m,9H); 4.65(m,1H) ; 4.20–4.40(m,2H); 3.96(m,1H); 3.60–3.70(m,2H); 3.0–3.30(m,2H). High Resolution Mass Spectrum: m/e=328.1015±0.8 ppm (calculated for $C_{18}H_{18}NO_3S$).

EXAMPLE 2

1-[2-(Phenylsulfonyl)benzoyl]-2-pyrrolidinecarboxaldehyde 0.6 g (1.7 mmol) of 1-[2-(phenylsulfonyl)benzoyl]-2-pyrrolidinemethanol in 0.73 ml (10 mmol) of dimethylsulfoxide (DMSO) and 20 ml methylene chloride was cooled to −70° C. 1.0 ml (6.8 mmol) of trifluoroacetic anhydride (TFAA) as added such that the temperature remained below −50° C. The reaction mixture was then stirred for 2 hours at between −50° and −70° C. 1.9 ml (14 mmol) of triethylamine was added and the mixture allowed to warm to 0° C. The reaction was quenched with water and the mixture was dried and evaporated to give an oil which was chromatographed on silica gel with chloroform to yield 0.2 g (34%) of the title compound. $^1$H NMR (CDCl$_3$) δ: 9.70(m,1H); 8.10–8.20(m,3H); 7.20–7.70(m,6H); 4.70(m,1H); 3.30–3.50 (m,2H); 1.70–2.30(m,4H). High Resolution Mass Spectrum: m/e=344.0951±0.6 ppm (calculated for $C_{18}H_{18}NO_4S$).

EXAMPLE 3

3-(2-Benzoylbenzoyl)-4-thiazolidinecarboxaldehyde 0.35 g (1.1 mmol) of the title compound of Example 1 was oxidized as described in Example 2. A standard work-up on the oil thereby obtained was performed by washing it with 5% sodium bicarbonate solution, 1N sodium hydroxide solution, 1N hydrochloric acid and brine. The organic phase was dried over magnesium sulfate and evacuated in vacuo to afford a residue. Purification of the residue by flash chromatography on silica gel (40:1/methylene chloride($CH_2C$):methanol(MeOH)) produced a second oil.

The second oil was triturated with ether to slowly crystallize the title compound which was collected via filtration to yield 70 mg (19%) of the title compound. $^1$H NMR ($CDCl_3$) δ: 9.50(s,1H); 7.0–8.0(m,9H); 5.10(m,1H); 4.3–4.6 (m,2H); 3.10–3.30(m,2H). Low Resolution Mass Spectrum: m/e=325(p).

EXAMPLE 4

2-[(4-(Hydroxymethyl)-3-thiazolidinyl)carbonyl]-N-(phenylmethyl)-benzamide 0.5 g (3.9 mmol) of the title compound of Preparation C was combined with 1.0 g (3.9 mmol) of 2-carboxy-N-phenylmethyl benzamide, 0.75 (3.9 mmol) 1-ethyl-3-(3-dimethylaminopropyl)carbodiimide, and 1 mol % catalytic 1-hydroxybenzotriazole in 50 ml of methylene chloride and stirred at room temperature for 18 hours. The resulting solution was washed with water followed by the methylene chloride being evaporated off. This resulted in a reaction product which was subjected to chromatographic purification on silica gel using 3:1/ethyl acetate:chloroform as the eluant to yield 0.3 g (22%) of the title compound. $^1$H NMR ($CDCl_3$) δ: 7.0–7.7 (m,9H) ; 3.8–4.7(m,6H); 2.9–3.6 (m, 3H). Low Resolution Mass Spectrum: m/e=339(p-17).

EXAMPLE 5

2-[(4-Formyl-3-thiazolidinyl)carbonyl]-N-(phenylmethyl)benzamide 1.1 g (3.1 mmol) of the title compound of Example 4 was oxidized as described in Example 2 using 1.1 ml (15 mmol) DMSO, 1.9 ml (12.4 mmol) TFAA, 2.2 ml (16 mmol) triethylamine in 25 ml methylene chloride. The crude product was chromatographed on silica gel with chloroform as the eluant to yield 0.3 g of material which was triturated with hot diisopropyl ether to yield 10 mg (1%) crystalline title product. 1H NMR ($CDCl_3$) δ: 9.60(s); 9.30(s,1H); 7.15–7.60 (m,10H); 4.10–5.20(m,8H). High Resolution Mass Spectrum: 326.1147±5.8 ppm ($C_{18}H_{18}N_2O_2S$).

EXAMPLE 6

3-(2-Benzoylbenzoyl)-4-thiazolidinemethanol 0.75 g (3.3 mmol) of the title compound of Preparation A, 0.39 g (3.3 mmol) of 2-phenylthiobenzoic acid, 0.64 g (3.3 mmol) of 1-ethyl-3-(3-dimethyl-aminopropyl)carbodiimide, 1 mol % of 1-hydroxybenzotriazole hydrate were combined and stirred at room temperature for 18 hours. The reaction mixture was washed with water, then dried and evaporated to an oil which was flash chromatographed on silica gel using chloroform as the eluant to yield 0.66 g (61%) of the title compound. $^1$H NMR ($CDCl_3$) δ:7.2–7.6(m,9H); 4.75 (m,1H); 4.24(s,2H); 3.80(m,2H); 3.20(m,2H). Low Resolution Mass Spectrum: m/e=331(p).

EXAMPLE 7

1-[2-(Phenylthio)benzoyl]-2-pyrrolidinemethanol

The title compound of Preparation A and 0.33 (2.3 mmol) of S(+)-2-pyrrolidinemethanol were reacted as described in Example 6 to afford 0.90 g (87%) of the title compound after chromatography on silica with chloroform. $^1$H NMR ($CDCl_3$) δ: 7.0–7.3 (m,9H); 4.48(m,1H); 4.10(M,1H); 3.40–3.65(m,2H); 3.06(m,2H); 1.90(m,1H); 1.35–1.70(m, 3H). Low Resolution Mass Spectrum: m/e=313.1 (p).

EXAMPLE 8

1-[2-(Phenylsulfonyl)benzoyl]-2-hydroxymethyl pyrrolidine

The title compound of Preparation B and S(+)-2-pyrrolidinemethanol were reacted as described in Example 6. Flash chromatography of the crude isolated material was performed on silica gel, using 1:1/ethyl acetate:chloroform as eluant, to yield 0.6 g (53%) of the title compound. $^1$H NMR ($CDCl_3$) δ: 8.0(m,3H); 7.40–7.60(m,5H); 7.18–7.38 (m,1H); 4.24(M,1H); 3.66(M,1H); 3.0–3.4(m,4H); 1.6–2.2 (m,6H). Low Resolution Mass Spectrum: m/e=346 (p+1).

EXAMPLE 9

3-[2-(Phenylsulfonyl)benzoyl]-4-thiazolidinemethanol

The title compound of Preparation B was reacted with the title compound of Preparation C. After chromatography on silica gel with 1:1/chloroform:ethyl acetate, the solution was evaporated under reduced pressure to yield 0.6 g (50%) of the title compound. $^1$H NMR ($CDCl_3$) δ: 7.9–8.1 (m,3H); 7.28–7.60(m,6H); 4.76 (m,1H); 4.0–4.4(m,4H); 3.24(d,J=2 Hz,2H). Low Resolution Mass Spectrum: m/e=363.1 (p).

EXAMPLE 10

1-[2-(Phenylsulfonyl)benzoyl]-4-thiazolidinecarboxyaldehyde

The title compound of Example 9 was oxidized as described in Example 2. The oil thus obtained was chromatographed on silica gel with chloroform to give a solution which was evaporated under reduced pressure to yield 0.2 g (33%) of the title compound as a foam. $^1$H NMR ($CDCl_3$) δ: 9.38(s,1H); 8.0(m,3H); 7.30–7.80(m,6H); 5.10(m,1H); 4.30–4.62(m,2H); 3.10–3.30(m,2H). High Resolution Mass Spectrum: m/e=362.0543±2.2 ppm (Calculated for $C_{17}H_{16}NO_4S_2$).

EXAMPLE 11

2-[[2-(Hydroxymethyl)-1-pyrrolidinyl]carbonyl]-1H-indole-1-carboxylic acid phenylmethyl ester A. 1H-indole-1,2-dicarboxylic acid, 1-(phenyl-methyl) ester. A first solution was formed when 0.5 g (3.1 mmol) of indole-2-carboxylic acid was dissolved in 20 ml of 1M THF cooled to −70° C. and 6.2 ml (6.2 mmol) lithium hexamethyldisilazane was added, keeping the temperature below −60° C. The reaction mixture was stirred for 30 minutes at −70° C., during which time a precipitate formed. A second solution was formed when 0.5 ml (3.3 mmol) benzyl chloroformate was added to 5 ml of THF and this solution was then added dropwise to the first solution to form a reaction mixture. The reaction mixture was stirred for 2 hours at a temperature less than −60° C., then allowed to warm to 0° C., quenched with water, and extracted with ethyl acetate. The extract was dried and evaporated to give an oil (0.9 g). The isolated material from the oil consisted of a mixture of starting material and product which was satisfactory for subsequent use without further purification.

B. 2-([2-(hydroxymethyl)-1-pyrrolidinyl]carbonyl]-1H-Indole-1-carboxylic acid phenylmethyl ester. 10.8 g (2.7 mmol of the title compound obtained in step A and S(+)-2-pyrrolidinemethanol were reacted as described in Example 6. This yielded 0.26 g (22%) of the title compound after chromatography on silica gel with chloroform. $^1$H NMR (CDCl$_3$) δ: 8.06 (d,J=3 Hz, 1H); 7.20–7.60(m,8H); 6.66(s, 1H); 5.38(s,1H); 4.44(bs,1H); 4.0(m, 1H); 3.84(m,1H); 3.55 (m,1H); 3.10–3.40(m,2H); 1.40–1.95(m,4H). Low Resolution Mass Spectrum: m/e=378.2 (p).

EXAMPLE 12

2-[(2-Formyl-1-pyrrolidinyl)carbonyl]-1H-indole-1-carboxylic acid phenylmethyl ester 0.26 g (0.7 mmol) of the title compound of step B of Example 11 was oxidized as described in Example 2 to give 0.17 g (65%) of the title compound after chromatography on silica gel with chloroform. $^1$H NMR (CDCl$_3$) δ: 9.26, 9.50(s,s,1H); 8.10(d,J=3 Hz,1H); 7.16–7.65 (m,8H); 4.36 (s,2H); 4.24(m,1H); 3.2–3.50(m,2H); 1.5–1.9(m,4H). Low Resultion Mass Spectrum: m/e=376.2 (p).

EXAMPLE 13

1-[2-(2-Pyridinylthio)benzoyl]-2-pyrrolidinemethanol

A. 2-(2-pyridinylthio)-benzoic acid. 3 g (0.019 mol) of thiosalicyclic acid, 1.8 ml (0.019 mol) of 2-chloropyridine, and 25 ml of dioxane were combined and heated at reflux for 18 hours to produce a tan solid which precipitated from solution. The reaction mixture was cooled to room temperature and the precipitated product collected by filtration, washed with ether, and dried. The yield of the title compound was 3.7 g (73%). $^1$H NMR (DMSO Cl$_6$) δ: 8.50(m, 1H); 8.28(s,1H); 7.85(m,2H); 7.20–7.50 (m,5H).

B. 1-[2-(2-Pyridinylthio)benzoyl]-2-pyrrolidinemethanol. 1.0 g (3.7 mmol) of the compound obtained in step A and S(+)-2-pyrrolidinemethanol were reacted as described in Example 6 to afford 0.61 g (53%) of product after purification by chromatography on silica gel with ethyl acetate. $^1$H NMR (CDCl$_3$) δ: 8.40(m,1H); 8.24(m,1H); 7.80(m,1H); 7.50(m,2H); 7.08–7.40(m,2H); 7.0(m,1H); 4.30–4.50(m, 3H); 3.90(bs,1H); 3.18(m,2H); 1.8–2.0(m,4H). Low Resolution Mass Spectrum m/e=313.1 (p).

EXAMPLE 14

2,3-dihydro-2-[[2-(hydroxymethyl)-1-pyrrolidinyl] carbonyl] 1H-Indole-1-carboxylic acid phenylmethyl ester A. 2,3-dihydro-1H-indole-1,2-dicarboxylic acid, 1-(phenylmethyl) ester. 10.0 g (0.0612 mol) of indoline-2-carboxylic acid was added to 100 ml of water and 1N NaOH was added to the solution until the pH was 8.0. To the resulting solution, 9.10 ml (0.0637 mol) carbobenzyloxychloride was added dropwise. The reaction mixture was stirred for 1 hour at room temperature while keeping the pH between 7.5 and 8.5 with addition of 1N NaOH. The mixture was then extracted with ether and the ether extracts discarded. The pH of the reaction mixture was then adjusted to 6.3 and extracted with ethyl acetate. The ethyl acetate extracts were combined, dried, and evaporated. The residue was chromatographed on silica gel eluting with 3:7/ethyl acetate:hexane. Fractions containing the desired material were combined and evaporated to yield 9.3 g (51%) of the title compound as a white amorphous solid. TLC (10:1/ chloroform:methanol) R$_f$=0.25. $^1$H NMR (CDCl$_3$) δ: 6.8–7.9(m,9H); 4.8–5.4(m,3H); 3.50(m,1H); 3.20(m,1H).

B. 2,3-dihydro-2-[[2-(hydroxy methyl)-1-pyrrolidinyl] carbonyl] 1H-indole-1-carboxylic acid phenylmethyl ester. 9.3 g (0.0313 mol) of the title compound of step A was mixed with 3.1 ml (0.0312 mol) of S-pyrrolidine-2-methanol, 5.0 g (0.0312 mol) of 1-ethyl-3-(3-dimethylaminopropyl)carbodiimide hydrochloride, and 4.2 g (0.0312 mol) of 1-hydroxybenzotriazole in 100 ml of methylene chloride and the resulting solution was stirred at room temperature for 16 hours. The methylene chloride solution was then extracted with 100 ml of water. To the resulting methylene chloride solution was added an additional 100 ml of water and the pH of the mixture adjusted to 9.5. The methylene chloride layer was again separated from the water, dried with sodium sulfate, and evaporated to yield 5.8 grams (49%) of the title compound as a white solid. TLC (1:1/ethyl acetate: chloroform): R$_f$=0.3. $^1$H NMR (CDCl$_3$) δ: 6.8–7.9(m,9H); 4.8–5.4 (m,3H); 2.8–3.6(m,7H); 1.40–2.0 (m,4H). High Resolution Mass Spectrum: 380.1742±0.66 ppm (calculated for C$_{22}$H$_{24}$N$_2$O$_4$).

EXAMPLE 15

2-[(2-Formyl-1-pyrrolidinyl)carbonyl]-2,3-dihydro-1H-indole-1-carboxylic acid phenylmethyl ester A solution of 3.0 ml (0.0345 mmol) oxalyl chloride in 240 ml of methylene chloride was cooled to −70° C. under a nitrogen atmosphere. To this solution was added 5.2 ml (0.0732 mol) of DMSO, keeping the temperature less than −60° C. The resulting solution was stirred for 10 minutes. To this was added a solution of 5.8 g (0.0153 mol) of the title compound of Example 14 dissolved in 5 ml of methylene choride, maintaining the temperature below −60° C. The reaction was stirred for 1 hour at −70° C. To this reaction mixture was added 10.7 ml (0.0763 mol) of triethylamine and the resulting mixture was allowed to warm to 0C. Approximately 25 ml of water was then added to the reaction mixture.

A standard work-up of the reaction mixture included the following. The methylene chloride layer was separated from the water layer, and the water layer was extracted two times with additional methylene chloride. The three methylene chloride extracts were combined, dried and evaporated to yield an oil. TLC (1:1 ethyl acetate: chloroform): R$_f$=0.35. $^1$H NMR (CDCl$_3$) δ: 9.0–9.4 (m,1H); 6.8–7.85(m,9H); 4.8–5.4(m,3H); 3.0–3.6(m,5H); 1.5–2.1 (m,4H). Low Resolution Mass Spectrum: m/e=378.1 (p+1).

EXAMPLE 16

1-[2-(2-Pyridinylthio)benzoyl]-2-pyrrolidinecarboxaldehyde 1.2 g (3.8 mmol) of the title compound of 1-[2-(2-pyridinylthio)benzoyl]-2-pyrrolidinemethanol was combined with 0.37 ml (4.2 mmol) of oxalyl chloride, 0.64 ml (9.0 mmol) of DMSO, 30 ml of methylene chloride, and 2.8 ml (20 mmol) triethylamine and oxidized according to the method used in Example 15. The methylene chloride extracts were combined, dried and evaporated to yield an oil. The oil was dissolved in ether, and to this solution was added ether saturated with HCl gas. The resulting precipitate was filtered and dried to yield 0.8 g of aldehyde (61%) as the hydrochloride salt. TLC (10:1/ethyl acetate: methanol): R$_f$=0.65. $^1$H NMR (free base)(CDCl$_3$) δ: 9.50, 9.22 (s,s,1H);

8.40(m,1H); 7.25–9.80(m,6H); 7.04(d,J=4 Hz;1H); 4.50(m, 1H); 3.60, 3.30(m,2H); 2.18(m,1H); 1.60–2.0(m,3H). Low Resolution Mass Spectrum: m/e=312.

EXAMPLE 17

2-[[2-(Hydroxymethyl)-1-pyrrolidinyl]carbonyl]1-piperidinecarboxylic acid phenylmethyl ester A. 1,2-piperidinedicarboxylic acid 1-(phenylmethyl) ester. 2.6 g (0.02 mol) of pipecolinic acid, 2.9 ml (0.02 mol) of carbobenzyloxychloride, and 50 ml of water were reacted as described in Example 14 while maintaining the pH of the solution at between 8.0 and 8.5 using 1N NaOH. The reaction time was 3 hours. A standard work-up procedure as was described in Example 3 was performed on the residue and afforded 3.5 g (67%) of acid as a colorless oil. TLC (3:1/chloroform:methanol) $R_f$=0.80. $^1$H NMR (CDCl$_3$) δ: 9.84(s,1H); 7.2–7.4(m,5H); 5.14(s,2H); 4.80–5.0(m,1H); 3.04(m,1H); 2.24(m,1H); 1.70(m,3H); 1.30(m,2H).

B. 2-[[2-(Hydroxymethyl)-1-pyrrolidinyl]carbonyl]1-piperidonecarboxylic acid phenylmethyl ester. 1.0 g (3.8 mmol) of the title compound of Step A was combined with 0.37 ml (3.8 mmol) of S(+)-2-pyrrolidinemethanol, 0.73 g (3.8 mmol) of 1-ethyl-3-(3-dimethylaminopropyl) carbodiimide hydrochloride, and 1 mol % of 1-hydroxybenzotriazole in 20 ml methylene chloride and stirred at room temperature for 18 hours. The resulting solution was washed with water, dried with sodium sulfate, and evaporated. The residue was chromatographed on silica gel using 5:1/chloroform:ethyl acetate as the eluant and yielded several product fractions containing the title compound. These product fractions were combined and evaporated to yield 0.75 g (57%) of the desired alcohol as an oil. TLC (2:1/ethyl acetate: chloroform): $R_f$=0.30. $^1$H NMR (CDCl$_3$) δ: 7.26(m,5H); 4.6–5.2 (m, 4H); 3.8–4.25 (m-2H); 3.20–3.60(m,6H); 1.4–2.1(m,8H).

EXAMPLE 18

2-[(2-Formyl-1-pyrrolidinyl)carbonyl]-1-piperidinecarboxylic acid phenylmethyl ester 0.75 g (2.2 mmol) of the title compound of Step B of Example 17 and 0.62 ml (8.8 mmol) of dimethylsulfoxide were combined in 20 ml dry THF and the solution cooled to −70° C. under nitrogen. 1.5 ml (1.1 mmol) of trifluoroacetic anhydride (TFAA) was added dropwise to the solution while maintaining the reaction temperature less than −65° C. The mixture was then stirred for 2 hours at −70° C. 3.0 ml (22 mmol) triethylamine (TEA) was then added to the solution, and the mixture was warmed to room temperature. To the reaction mixture was then added 25 ml of water, and the resulting mixture was extracted several times with ethyl acetate. The ethyl acetate extracts were combined, dried using sodium sulfate, and evaporated to yield an oil. The oil was chromatographed on silica gel using chloroform as resulting mixture was extracted several times with ethyl acetate. The ethyl acetate extracts were combined, dried using sodium sulfate, and evaporated to yield an oil. The oil was chromatographed on silica gel using chloroform as an eluant to yield several product fractions containing the title compound. The product fractions were combined and evaporated to yield 0.11 g (14%) of the desired aldehyde as an oil. TLC (1:1/ethyl acetate:chloroform): $R_f$=0.45. $^1$H NMR (CDCl$_3$) δ: 9.42(m,1H); 8.32(m,5H); 4.6–5.2(m,4H); 3.2–4.6(m,4H); 1.8–2.2(m,10H). Low Resolution Mass Spectrum: m/e=345.2 (p+1).

EXAMPLE 19

2-[[2-(Hydroxymethyl)-1-pyrrolidinyl]carbonyl]-cyclohexanecarboxylic acid phenylmethyl ester A. Trans 1,2-cyclohexanedicarboxylic acid mono (phenylmethyl)ester. 5.0 g (0.032 mol) of trans-1,2-cyclohexanedi-carboxylic anhydride was dissolved in 20 ml of benzyl alcohol and the solution heated to 80° C. for 1.5 hours. The solution was then cooled to room temperature and poured into 50 ml of water. The pH was adjusted to 9.5 and the mixture extracted with ethyl acetate. The ethyl acetate extracts were discarded. The pH of the aqueous phase was then adjusted to 2.5 and the solution extracted again several times with ethyl acetate. The second ethyl acetate extracts were combined, dried using sodium sulfate, and evaporated to yield a residue that was chromatographed on silica gel using 2:1/hexane:ethyl acetate as the eluant. Fractions containing the title compound were combined and evaporated to yield 2.8 g (33%) of the desired acid as an oil. TLC (2:1/hexane:ethyl acetate): $R_f$=0.40. $^1$H NMR (CDCl$_3$) δ: 7.25(m,5H); 5.06(m,2H); 2.60(m,2H); 2.08(m,2H); 1.75 (m,2H); 1.70(m,4H).

B. 2-[[2-(Hydroxymethyl)-1-pyrrolidinyl]carbonyl]-cyclohexanecarboxylic acid phenylmethyl ester. 2.8 g (0.0106 mol) of the title compound of Step A was combined with 1.05 ml (0.0106 mol) of S(+)-2-pyrrolidinemethanol, 2.0 g (0.0106 mol) of 1-ethyl-3-(3-dimethylaminopropyl) carbodiimide hydrochloride, and 1.4 g (0.0106 mol) of 1-hydroxybenzotriazole in 25 ml methylene chloride and stirred at room temperature for 48 hours. The reaction mixture was washed with 40 ml of 5% HCl and 40 ml of 5% NaOH. The methylene chloride solution was dried and evaporated and the resulting residue was chromatographed on silica gel using 1:1/acetone:hexane as the eluant to yield 1.2 g (33%) of the title compound as an oil. TLC (3:7/acetone:hexane): $R_f$=0.5. $^1$H NMR (CDCl$_3$) δ: 8.25(m,5H); 5.02(m,2H); 4.04(m,1H); 3.25(m,4H); 2.85(m,1H); 2.60(m, 1H); 2.10m(1H); 1.60–2.0 (m,7H); 1.2–1.6(m,4H). Low Resolution Mass Spectrum: m/e=346.2 (p+1).

EXAMPLE 20

2-[(2-Formyl-1-pyrrolidinyl)carbonyl]-cyclohexanecarboxylic acid phenylmethyl ester A solution of 1.24 ml (2.75 mmol) oxalyl chloride in 15 ml of methylene chloride was cooled to −70° C. under a nitrogen atmosphere. To this solution was added 0.41 ml (5.83 mmol) of dimethylsulfoxide, keeping the temperature −60° C. The resulting solution was stirred for 10 minutes. To this was added a solution of 0.42 g (1.21 mmol) of the title compound of Example 19 dissolved in 5 ml of methylene chloride, maintaining the temperature below −60° C. The reaction was stirred for 1 hour at −70° C. To this reaction mixture was added 0.84 ml (6.07 mmol) of triethylamine and the resulting mixture was allowed to warm to 0° C. Approximately 25 ml of water was then added to the reaction mixture. The methylene chloride layer was separated from the water layer, and the water layer extracted two times with additional methylene chloride. The three methylene chloride extracts were combined, dried, and evaporated to yield 320 mg (76%) of the title compound as an oil. TLC (3:7/acetone:hexane): $R_f$=0.6. $^1$H NMR (CDCl$_3$) δ: 9.06; 9.32(m,1H); 8.25(m,5H); 4.8–5.1(m,2H); 4.1–4.3(m, 1H); 3.2–3.7(m,2H); 2.75(m,1H); 2.60(m,1H); 2.10(m,1H); 1.60–2.10(m,7H); 1.10–1.50(m,4H). Low Resolution Mass Spectrum: m/e=344.2 (p+1).

EXAMPLE 21

2-[(2-(Hydroxymethyl)-1-pyrrolidinyl)carbonyl]-cyclohexanecarboxylic acid phenylmethyl ester A. cis 1,2-cyclohexamedicarboxylic acid, mono (phenylmethyl)ester. 5.0 g (0.032 mol) of cis-1,2-cyclohexanedicarboxylic anhydride was reacted with 20 ml of benzyl alcohol as described in Part A of Example 19 to yield 5.8 g (68%) of the title compound. TLC (3:7/acetone:hexane): $R_f$=0.15. $^1$H NMR (CDCl$_3$) δ: 8.24(m,5H); 5.06(m,2H); 2.80 (m,2H); 2.0(m,2H); 1.75(m,2H); 1.40(m, 4H).

B. 2- [(2-(hydroxymethyl)-1-pyrrolidinyl)carbonyl]-Cyclohexanecarboxylic acid phenylmethyl ester. 2.0 g (0.015 mol) of the title compound of Step A was reacted with 1.5 ml (0.015 mol) of S(+)-2-pyrrolidinemethanol, 2.9 g (0.015 mol) of 1-ethyl-3-(3-dimethylaminopropyl) carbodiimide hydrochloride, and 2.1 g (0.015 mol) of 1-hydroxybenzotriazole in 25 ml methylene chloride as described previously in Part B of Example 19 to yield 1.2 g (23%) of the title compound as an oil. TLC (3:7/acetone:hexane): $R_f$=0.4. $^1$H NMR (CDCl$_3$) δ: 8.25(m,5H); 4.8–5.15(m,2H); 4.50(m,1H); 4.0(m,1H); 3.2–3.7(m,4H); 2.95–3.10(m,1H); 2.4–2.6(m,1H); 2.2–2.4(m,1H); 1.2–2.0 (m,11H).

EXAMPLE 22

Cis-2-[[2-(hydroxymethyl)-1-pyrrolidinyl]carbonyl]-cyclohexanecarboxylic acid phenymethyl ester 500 mg (1.44 mmol) of the title compound of Step B of Example 21 was reacted with 0.285 ml (3.27 mmol) of oxalyl chloride, 0.493 ml (6.94 mmol) of DMSO, and 1.0 ml (7.3 mmol) of triethylamine in 10 ml of methylene chloride as described previously in Example 15 to yield 250 mg (50%) of the title compound as an oil. TLC(3:7/acetone:hexane): $R_f$=0.35. $^1$H NMR (CDCl$_3$) δ: 9.10; 9.32 (m,1H); 8.25m(5H); 4.86–5.20(m,2H); 4.10–4.30(m,1H); 3.4–3.6(m,2H); 3.10 (m,1H); 2.20–2.60(m,2H); 1.10–2.20 (m,11H). Low Resolution Mass Spectrum: m/e=344.1 (p+1).

EXAMPLE 23

3-[(2-Hydroxymethyl-1-pyrrolidinyl)carbonyl]-7-oxabicyclo-[2.2.1]heptane-2-carboxylic acid phenymethyl ester A. 7-oxabicyclo[2.2.1]heptane-2,3-dicarboxylic acid, mono (phenylmethyl)ester. 4.7 g (0.03 mol) of 7-oxabicyclo [2.2.1]-heptane-2,3-dicarboxylic anhydride was reacted with 25 ml of benzyl alcohol as described in Part A of Example 19 to yield 2.7 g (33%) of the title compound as an oil. TLC (ethyl acetate): $R_f$=0.33. $^1$H NMR (CDCl$_3$) δ: 8.26 (s,5H); 4.8–5.2(m,4H); 3.0(s,2H); 1.80(m,2H); 1.50(m,2H).

B. 3-[(2-Hydroxymethyl-1-pyrrolidinyl)carbonyl]-7-oxabicyclo[2.2.1]heptane-2-carboxylic acid phenymethyl ester. 500 mg (1.81 mmol) of the title compound of Step A was reacted with 183 mg (1.81 mmol) of S-pyrrolidine-2-methanol, 244 mg (1.81 mmol) of 1-hydroxybenzotriazole, and 346 mg (1.81 mmol) of 1-ethyl-3-(3-dimethylaminopropyl)carbodiimide hydrochloride in 30 ml of methylene chloride as described in Part B of Example 19 to yield 429 mg (67%) of the title compound as an oil. TLC (1:1/hexane:ethyl acetate): $R_f$=0.25. $^1$H NMR (CDCl$_3$) δ: 8.25(s,5H); 4.8–5.2 (m,4H); 3.75(m,1H); 3.30–3.60(m,4H); 3.0(s,2H); 1.6–2.0 (m,4H). Low Resolution Mass Spectrum: m/e=360.1 (p+1).

EXAMPLE 24

2-[(2-Formyl-1-pyrrolidinyl)carbonyl]-cyclohexanecarboxylic acid phenymethyl ester 320 mg (0.89 mmol) of the title compound of Example 23 was reacted with 0.085 ml (0.97 mmol) of oxalyl chloride, 0.139 ml (1.96 mmol) of DMSO, and 0.62 ml (4.45 mmol) of triethylamine in 10 ml methyl chloride as described previously in Example 16 to yield 100 mg of the desired aldehyde as an oil. TLC (10:1/chloroform:ethyl acetate): $R_f$=0.25. $^1$H NMR (CDCl$_3$) δ: 9.26–9.35(m,1H); 8.35(m, 5H); 4.6–5.0(m,4H); 3.40(m,2H); 2.96(m,2H); 1.6–2.0(m, 7H); 1.40(m,2H). Low Resolution Mass Spectrum: m/e= 358.1 (peak +1).

EXAMPLE 25

1-(2-Benzoylbenzoyl)-L-proline methyl ester 6.20 g (27.5 mmol) of o-benzoylbenzoic acid was dissolved in 150 ml of methylene chloride at 25° C. under a nitrogen atmosphere. The solution was cooled to 10° C. and 4.08 g (30.2 mmol) of 1-hydroxybenzotriazole hydrate was added, followed by 5.0 g (30.2 mmol) of L-proline methyl ester HCl and followed by 6.22 g (30.2 mmol) of N,N'-diisopropylethylamine. Lastly, 6.22 g (30.2 mmol) N,N'-dicyclohexylcarbodiimide (DCC) was added which produced a slight exothermic reaction and the mixture was then stirred for 12 hours, after which time tlc analysis indicated complete consumption of starting material. A standard work-up was performed which involved removing precipitated urea by filtration and washing the filtrate with 5% sodium bicarbonate solution, 1N sodium hydroxide solution, 1N hydrochloric acid and brine. The organic phase was dried over magnesium sulfate and evaporated in vacuo to afford a yellow residue. Purification by flash chromatography on silica gel (40:1/methylene chloride:methanol) gave a yield of 6.4 g (69%) of the title compound as a cloudy gum which crystallized on standing. TLC (90:10/CH$_2$Cl$_2$:MeOH): $R_f$=0.80. mp=128–130. $^1$H NMR (CDCl$_3$) δ: 7.40–7.85(m, 9H); 4.25–4.55(m,1H); 3.40–3.75(m,5H); 1.85–2.40(m,4H). I.R. (KBr): 1622, 1661, 1739, 1745 cm$^{-1}$. Standard Combustion Analysis: C,71.20; H,5.68; N,4.15. Found: C,70.63; H,5.53; N=4.36. High Resolution Mass Spectrum: m/e= 338.1384±0.8 ppm (calculated for C$_{20}$H$_{20}$NO).

EXAMPLE 26

1-(2-Benzoylbenzoyl)-L-proline 1,1-dimethylethyl ester 6.78 g (30mmol) of o-benzoylbenzoic acid, 5.13 g (30 mmol) of L-proline t-butyl ester, 4.05 g (30 mmol) of 1-hydroxybenzotriazole hydrate and 6.18 g (30 mmol) of DCC in 100 ml methylene chloride were reacted in the manner described in Example 25 for the coupling of o-benzoylbenzoic acid with L-proline t-butyl ester. A standard work-up as described in Example 25 afforded a viscous gum which was purified by flash chromatography on silica gel with 40:1/methylene chloride:methanol as eluant to give an amorphous solid. The isolated yield of the title compound was 8.6 g (76%). TLC (90:10/CH$_2$Cl$_2$:MeOH): $R_f$=0.80. $^1$H NMR (CDCl$_3$) δ: 7.30–7.80(m,9H,); 4.06–4.38(m,1H); 3.36–3.65(m,2H); 1.78–2.32(m,4H); 1.32(s),1.43(s,9H). I.R. (KBr): 1595, 1627, 1661, 1733 cm$^{-1}$. Low Resolution Mass Spectrum: 380 (p+1). Standard Combustion Analysis Calculated: C,72.80; H,6.64; N,3.69. Found: C,72.37; H,6.59; N,3.76.

EXAMPLE 27

1-(2-Benzoylbenzoyl)-2-(trifluoroacetyl)-pyrrolidine 4.0 g (10.6 mmol) of the title compound of Example 25 was dissolved in 50 ml of methylene chloride at room temperature under an atmosphere of nitrogen. 20 ml (260 mmol) trifluoroacetic acid (TFA) was added and the solution refluxed for 2 hours to hydrolyze the ester. Solvent and excess TFA were then removed under reduced pressure, the residue was redissolved in 22.5 ml (159 mmol) of trifluoroacetic anhydride (TFAA), and the solution refluxed for 12 hours. The TFAA was evaporated under high vacuum at 80° C. to give an impure yellow gum. Flash chromatography on silica gel with 100% ether afforded 80 mg (2%) of the title compound as a yellow foam. TLC (Ether): $R_f$=0.50. $^1$H NMR (CDCl$_3$) δ: 7.32–7.84(m,9H); 4.30–4.96(m,1H); 3.20–3.54 (M,2H); 1.68–2.48(m,4H). High Resolution Mass Spectrum: 376.1170±0.9 ppm (calculated for $C_{20}H_{17}NO_3F_3$). 2,4-DNP test: positive

EXAMPLE 28

1-(2-Benzoylbenzoyl)-(S)-2-pyrrolidinemethanol 6.78 g (30 mmol) o-benzoylbenzoic acid and 2.96 ml (30 mmol) of S(+)-2-pyrrolidinemethanol were reacted with 4.05 g (30 mmol) 1-hydroxybenzotriazole hydrate and 6.18 g (30 mmol) of DCC in 150 ml methylene chloride as described in Example 25 for the coupling of o-benzoylbenzoic acid with L-proline methyl ester. The crude reaction mixture was washed with 5% sodium bicarbonate solution, dried over anhydrous magnesium sulfate, and the solvent removed in vacuo to afford a yellow residue. Flash chromatograohy on silica gel (20:1/methylene chloride:methanol) afforded the title compound which crystallized from ethyl acetate as a white solid (3.99 g (43%)) by the addition of ether until crystallization took place. TLC (90:10/$CH_2Cl_2$:MeOH): $R_f$=0.50. mp=113–114. $^1$H NMR (CDCl$_3$) δ: 7.35–7.80 (9m,5H); 4.40–4.50(m,1H); 3.15–4.20(m,5H); 1.55–2.15(m,4H). I.R. (KBr): 1589, 1603, 1660 cm$^{-1}$. Standard Combustion Analysis Calculated: C,73.77; H,6.19; N,4.53. Found: C,73.40; H,6.16; N,4.41. High Resolution Mass Spectrum: 309.1378±1.3 ppm (calculated for $C_{19}H_{19}NO_3$).

EXAMPLE 29

1-(2-Benzoylbenzoyl)-2-pyrrolidinecarboxaldehyde 1.03 g (3.3 mmol) of the title compound of Example 28 was dissolved in 50 ml of methylene chloride at room temperature under a nitrogen atmosphere. 3.76 g (10.0 mmol) of pyridinium dichromate and 4 g powdered 4A molecular sieves were added, and the reaction was allowed to stir at ambient temperature for 3 hours. The sieves and precipitated salts were then removed by filtration and the filtrate washed with water, 5% sodium bicarbonate solution and 1N HCl solution. The organic phase was dried over magnesium sulfate, filtered and evaporated to give a dark brown oil which crystallized on standing. The crude product was heated in 1:1/ethyl acetate:methylene chloride with enough methanol added for the crude product to go into solution and decolorized with activated charcoal. The title compound was recrystallized from 1:1/ethyl acetate:ether to yield 0.24 g (24%). TLC: (90:10/$CH_2Cl_2$:MeOH): $R_f$=0.80. mp=158–160. $^1$H NMR (CDCl$_3$) δ: 9.42(s); 9.32 (s,1H); 7.32–7.85(m,9H); 4.20–4.50(m,1H); 3.32–3.70(m,2H) 1.70–2.30(m,4H). IR (KBr): 1578, 1590, 1613, 1725 cm$^{-1}$. Standard Combustion Analysis Calculated: C,74.25; H,5.58; N,4.56. Found: C,73.66; H,5.64; N,4.65. High Resolution Mass Spectrum: m/e=308.1291±0.4 ppm (calculated for $C_{19}H_{18}NO_3$). 2,4-DNP test: positive.

EXAMPLE 30

1-(2-Naphthalenylcarbonyl)-benzoyl)-(S)-2-pyrrolidinemethanol 8.28 g (30 mmol) of 2-(1-naphthoyl)benzoic acid was reacted with 2.96 ml (30 mmol) of S(+)-2-pyrrolidinemethanol, 4.05 g (30 mmol) 1-hydroxybenzotriazole hydrate, and 6.18 g (30 mmol of DCC in 150 ml methylene chloride as previously described in Example 25 for the coupling of benzoic acid with S(+)-2-pyrrolidinemethanol. The crude reaction mixture was purified by flash chromatography on silica gel (15:1/methylene chloride: methanol) to afford the title compound as a viscous gum which could not be crystallized. The isolated yield of the title compound was 7.80 g (72%). TLC (90:10/$CH_2Cl_2$:MeOH): $R_f$=0.35. $^1$H NMR (CDCl$_3$) δ: 7.32–8.40(m,11H); 4.02–4.17(m, 1H); 3.24–3.84 (m,4H); 1.54–2.16(m,4H). High Resolution Mass Spectrum: 359.1530±0.9 ppm (calculated for $C_{23}H_{21}NO_3$).

EXAMPLE 31

1-[2-(1-Naphthalenyl-carbonyl)benzoyl]-2-pyrrolidinecarboxaldehyde 1.40 g (3.9 mmol) of the title compound of Example 30 was oxidized using 6.01 g (16 mmol) of pyridinium dichromate and 6 g powdered 4A molecular sieves in 50 ml of methylene chloride as described in Example 29. The reaction mixture was filtered, washed with water, 1N HCl and saturated sodium bicarbonate solution, and dried over magnesium sulfate. After filtration the dark solution was decolorized with activated charcoal. Removal of solvent in vacuo afforded a light tan solid which was digested in ether and collected by filtration. This crude solid was further purified by flash chromatography on silica gel (1:1/ethyl acetate:methylene chloride) to give a colorless gum. The gum was crystallized from ether with isopropanol added to solubilize the gum in the ether. The title compound and was then recrystallized from the ethyl acetate to give a pure white solid (210 mg, 15%). TLC (90:10/$CH_2Cl_2$:MeOH): $R_f$=0.70. mp=158–160. $^1$H NMR (CDCl$_3$) δ: 9.47(s), 9.32(s,1H); 7.35–8.45(m,11H); 4.25–4.40(m,1H) 3.30–3.70(m,2H) 1.70–2.35(m,4H). I.R. (KBr): 1590, 1607, 1654, 1726 cm$^{-1}$. Low Resolution Mass Spectrum: m/e=358.2 (p+1). Standard Combustion Analysis Calculated: C,77.29; H,5.36; N,3.92. Found: C,76.27; H,5.33; N,3.83. 2,4-DNP: test Positive.

EXAMPLE 32

1-[(9-Oxo-9H-fluoren-1-yl)carbonyl]-2-pryrrolidinemethanol 2.24 g (10 mmol) of 9-fluorenone-1-carboxylic acid, 1.0 ml (10 mmol) of S(+)-2-pyrrolidinemethanol, 1.35 g (10 mmol) of 1-hydroxybenzotriazole hydrate, and 2.06 g (10 mmol) of DCC in 50 ml methylene chloride were reacted as described in Example 25 for the coupling of the carboxylic acid and S(+)-2-pyrrolidinemethanol. The product was purified by flash chromatography on silica gel (15:1/methylene chloride:methanol) to give a yellow gum. The gum was dissolved in a solution of ethyl acetate with an isopropanol concentration of less than 5% and ether added to cause crystallization. The yellow solid thus obtained was collected by filtration, washed with ether, and dried. The isolated yield of the title compound was 2.40 g (78%). TLC (90:10/ $CH_2Cl_2$:MeOH):$R_f$=0.50. mp=138–140. $^1$H NMR ($CDCl_3$) δ:7.10–7.60 (m,7H); 3.05–4.60(m,6H); 1.50–2.30(m,4H). IR (KBr):1597, 1606, 1709 cm$^{-1}$. Low Resolution Mass Spectrum: m/e=308.2 (p+1). Standard Combustion Analysis Calculated: C,74.25; H,5.58, N,4.56. Found: C,73.73; H,5.72; N,5.03.

EXAMPLE 33

1-[(9-oxo-9H-fluoren-1-yl)carbonyl]-2-pyrrolidinecarboxaldehyde 0.50 ml (5.5 mmol) of oxalyl chloride in 25 ml of methylene chloride was cooled to –60° C. under a nitrogen atmosphere. A solution of 0.85 ml (11 nmol) of DMSO in 5 ml of methylene chloride was added dropwise such that the temperature remained below –50° C. The mixture was stirred for 2 minutes and then 1.54 g (5 mmol) of the title compound of Example 32 dissolved in 10 ml of methylene chloride was added over a period of 5 minutes. Stirring was continued for an additional 15 minutes at –50° C. and then triethylamine was added. After 5 minutes, the reaction was allowed to warm to room temperature and quenched with water, 1N HCl, 5% sodium bicarbonate solution and brine. The solution was dried over magnesium sulfate, filtrated and evaporated to give a yellow gum which was flash chromatographed on silica gel (100% ethyl acetate) to give pure product. The aldehyde, isolated as a gum, was crystallized from isopropanol/ethyl acetate. The yield of crystallized material was 0.260 g (17%). TLC (EtOAc):$R_f$=0.35. mp=134–136. $^1$H NMR ($CDCl_3$) δ: 9.30(s,1H); 7.08–7.70 (m,7H); 4.38–4.90(m,1H); 3.25–4.13 (m,2H); 1.76–2.35(m, 4H). I.R. (KBr): 1584, 1608, 1629, 1704, 1731 cm$^{-1}$. High Resolution Mass Spectrum: 276.1004±2 ppm (calculated for $C_{18}H_{14}NO_2$). Standard Combustion Analysis Calculated: C,74.74; H,4.95; N,4.59. Found: C,73.78; H,5.03; N,4.80. 2,4-DNP test: Positive.

EXAMPLE 34

(S)-1-(Phenoxybenzoyl)-2-pyrrolidinemethanol 2.14 g (10 mmol) of 2-phenoxybenzoic acid, 1.35 g (10 mmol) of 1-hydroxybenzotriazole hydrate, 2.0 ml (20 mmol) of A and 1.92 g (10 mmol) 1-ethyl-3-(3-dimethyl-aminopropyl)carbodiimide HCl were reacted as described in Example 25, except that a water soluble carbodiimide was used in place of DCC. The title compound was obtained in pure form as a colorless gum without chromatographic purification and the yield was 2.90 g (98%). TLC (90:10/ $CH_2Cl_2$:MeOH):$R_f$=0.80. $^1$H NMR ($CDCl_3$) δ: 6.80–7.45 (m,9H); 4.60–4.95(m,1H); 3.30–3.80(m,4H); 1.50–2.20(m, 4H).

EXAMPLE 35

1-(2-Phenoxybenzoyl)-2-pyrrolidinecarboxaldehyde 1.20 g (4 mmol) of the title compound of Example 34 was dissolved in 15 ml of DMSO at room temperature under a nitrogen atmosphere. 9.10 ml (66 mmol) of triethylamine was added to give a two-phase mixture. Then, 2.10 g (13.2 mmol) sulfur trioxide-pyridine complex in 15 ml DMSO was added dropwise and the resultant brown mixture was stirred for 12 hours, cooled to 0° C., quenched with cold water, and acidified to pH 0. The reaction mixture was then extracted with two portions of methylene chloride which were combined and washed with 1N HCl, 5% sodium bicarbonate and dried over magnesium sulfate. Filtration and evaporation of the solvent afforded the title compound as a yellow gum which was obtained in quantitative yield and found to be pure by tlc analysis (silica gel: 100% ethyl acetate). TLC (ethyl acetate): $R_f$=0.60. 2,4-DNP test: positive.

EXAMPLE 36

(S)-2-[(2-(Hydroxymethyl)-1-pyrrolidinyl)carbonyl]-N-(phenylmethyl)-benzamide

A. 2-[(phenylmethyl)amino]carbonyl]-benzoic acid. 5.45 ml (50 mmol) of benzylamine was added to a solution of 7.40 g (50 mmol) phthalic anhydride in 100 ml of benzene at room temperature under a nitrogen atmosphere. The mixture was heated at reflux for 12 hours, cooled, and the solvent removed under reduced pressure. The residue was digested in ether and the title compound was collected by filtration as a white solid (8.90 g, 70%). TLC (90:10/ $CH_2Cl_2$:MeOH): $R_f$=0.20. $^1$H NMR (DMSO $D_6$) δ:8.80–8.92(m,1H); 7.16–7.80 (m,9H); 4.38–4.52(m,2H).

B. (S)-2-[(2-(Hydroxymethyl)-1-pyrrolidinyl)carbonyl]-N-(phenylmethyl)-Benzamide. 7.65 g (30 mmol) of the title compound of Part A was reacted with 4.05 g (30 mmol) of 1-hydroxybenzotriazole hydrate, 3.0 ml (30 mmol) of S(+)-2-pyrrolidinemethanol and 6.18 g (30 mmol) of DCC in 100 ml methylene chloride as described in Example 25 for the coupling of the acid and the S(+)-2-pyrrolidinemethanol. Impure material was obtained as a white solid. Isopropanol was added and insoluble solids removed by filtration. The filtrate was evaporated to give the title compound as an amorphous foam which was pure by tlc analysis (silica gel: 9:1/methylene chloride:methanol) gave an isolated yield of 5.8 g (57%). TLC (90:10/$CH_2Cl_2$:MEOH): $R_f$=0.40. $^1$H NMR ($CDCl_3$) δ: 7.16–7.64(m,9H); 4.00–4.83(m,4H); 3.02–3.85(m,3H); 1.60–2.12(m,4H). I.R. (KBr) 1428, 1452, 1494, 1535, 1573, 1617, 1636, 1642, 1717 cm$^{-1}$. High Resolution Mass Spectrum: 339.170±0.6 ppm (calculated for $C_{20}H_{23}N_2O_3$).

EXAMPLE 37

2-[(2-Formyl-1-pyrrolidinyl)carbonyl]-N-(phenylmethyl)benzamide 1.35 g (4.0 mmol) of the title compound of Example 36 was reacted with 2.10 g (13.2 mmol) of sulfur trioxidepyridine complex, 9.2 ml (66 mmol) of triethylamine, and 20 ml of DMSO as described in Example 35. The standard work-up as described in Example 3 afforded a gum which was crystallized from 1:1/ether:pentane to give 1.0 g (75%) of the title compound as an off-white solid. TLC (90:10/ $CH_2Cl_2$:MeOH): $R_f$=0.35. mp=140–142. $^1$H NMR ($CDCl_3$) δ: 9.56(s); 9.25(s,1H); 7.08–7.70(m,9H); 4.10–4.70(m,3H); 2.85–3.60(m,2H); 1.50–2.20(m,4H). I.R. (KBr): 1422, 1451, 1530, 1573, 1598, 1632, 1728 cm$^{-1}$. Low Resolution Mass Spectrum: m/e=337.2 (p+1). Standard Combustion Analysis Calculated: C,69.54; H,6.13; N,8.11. Found: C,69.99; H,6.12; N,8.23. 2,4-DNP test: positive.

EXAMPLE 38

(S)-2-[[2-(Hydroxymethyl)-1-pyrrolidinyl]carbonyl] phenyl]benzamide

A. N-[2-carboxyphenyl)-benzamide. 1.40 ml (12 mmol) benzoyl chloride and 20 mg N,N'-dimethylaminopyridine (DMAP) were added to 1.51 g (10 mmol) of methyl anthranilate in 20 ml of pyridine at ice bath temperature under a nitrogen atmosphere. The reaction mixture was stirred for 2 days at room temperature, quenched with water, and acidified to pH 1–2 with 4N HCl solution. The mixture was then extracted with two portions of methylene chloride, and the organic extracts washed with 4N HCl, 1N sodium hydroxide and brine. The washed solution was dried over magnesium sulfate, filtered, and evaporated under reduced pressure to give a tan residue. The crude product was saponified by refluxing for 2 hours in aqueous ethanolic potassium hydroxide solution (5–10% ethanol in $H_2O$ and 3–5 equivalents of KOH to saturate the solution). The reaction mixture was then cooled, ethanol was removed in vacuo and water was added. The pH was adjusted to 1 with 4N HCl and the precipitated title compound collected by filtration and dried to yield an off-white solid (2.10 g, 87%). TLC (ethyl acetate): $R_f$=0.15. $^1$H NMR (DMSO $D_6$) δ: 12.28 (s,1H); 7.15–8.75(m,9H).

B. (S)-2-[[2-(hydroxymethyl)-1-pyrrolidinyl]carbonyl]phenyl]-Benzamide. 2.10 g (8.71 mmol) of the title compound of step A was reacted with 1.18 g (8.71 mmol) of 1-hydroxybenzotriazole hydrate, 0.86 ml( 8.71 mmol) of S(+)-2-pyrrolidinemethanol, and 1.80 g (8.71 mmol) of DCC, in 50 ml 1:1/methylene chloride:THF, as described in Example 25. The standard work-up described in Example 25 afforded a light yellow, viscous gum which was purified by flash chromatography on silica gel with 100% ethyl acetate as eluant. The title compound was obtained as a foam which was digested in ether, filtered, and dried to afford a white solid (0.500 g, 18%). TLC (90:10/$CH_2Cl_2$:MeOH): $R_f$=0.40. mp=142–144. $^1$H NMR (DMSO $D_6$) δ: 7.20–8.702(m,9H); 4.70–4.88(m,1H); 4.03–4.20(m,1H); 3.20–3.68(m, 5H); 1.45–2.03(m,4H). High Resolution Mass Spectrum: m/e= 307 (calculated for $C_{19}H_{19}N_2O_2$).

EXAMPLE 39

1-[(2-Carboxy-1-cyclopenten-1-yl)carbonyl]-L-proline, 2-methyl ester 2.76 (20 mmol) of 1-cyclopentene-1,2-dicarboxylic anhydride was dissolved in 50 ml of THF at 25° C. under a nitrogen atmosphere. The solution was cooled to 10° C. and 3.31 g (20 mmol) of L-proline methyl ester HCl was added, followed by 2.78 ml (20 mmol) $Et_3N$, which produced a slight exothermic reaction. The mixture was heated at reflux for 12 hours, cooled and the solvent removed under reduced pressure. The residue was dissolved in methylene chloride and the solution was washed with 1N hydrochloric acid and brine. The organic phase was then dried over magnesium sulfate and evaporated in vacuo to afford the title compound which crystallized from methylene chloride/ether as an off-white solid (4.20 g; 79%). TLC (90:10/$CH_2Cl_2$:MeOH): $R_f$=0.35. $^1$H NMR δ: 8.15–8.42(bs,1H); 4.35–4.60(m,1H); 3.38–3.76(m,5H); 2.48–2.98(m,4H); 1.70–2.32(m,6H).

EXAMPLE 40

1-[(2-[(Phenylmethyl)amino]carboyl]-1-cyclopenten-1-yl)carbonyl]-L-proline methyl ester 4.20 g (15.7 mmol) of the title compound of Example 39 was reacted with 1.72 ml (15.7 mmol) of benzylamine and 3.02 g (15.7 mmol) of 1-ethyl-3-(3-dimethylaminopropyl) carbodiimide HCl, in 50 ml methylene chloride as described in Example 34. A work-up as described in Example 15 afforded the desired product in pure form as a yellow gum without chromatographic purification. The yield was 3.40 g (61%). TLC (90:10/$CH_2Cl_2$:MeOH): $R_f$=0.75. $^1$H NMR ($CDCL_3$) δ: 7.15–7.36(m,6H); 4.26–4.63(m,3H); 3.32–3.73 (m,5H); 2.58–2.84(m,4H); 1.72–2.22(m,6H).

EXAMPLE 41

2-[[2-(Hydroxymethyl)-1-pyrrolidinyl]carbonyl]-N-phenylmethyl)-1-cyclopentene-1-carboxamide 3.40 g (9.6 mmol) of the title compound of Example 40 was dissolved in 50 ml of ethanol at 25° C. under a nitrogen atmosphere. The solution was cooled to 10° C. and 3.63 g (96.0 mmol) of sodium borohydride was added. The mixture was heated at reflux for 2 hours, after which thin layer chromatography analysis indicated complete consumption of starting material. The mixture was then cooled and the solvent removed under reduced pressure. The residue was dissolved in methylene chloride and the solution washed with water and brine. The organic phase was dried over magnesium sulfate and evaporated in vacuo to afford the title compound in pure form as a light yellow gum with a yield of 2.80 g (89%). TLC (90:10/$CH_2Cl_2$:MeOH): $R_f$=0.40. $^1$H NMR ($CDCl_3$) δ:7.15–7.45(m,6H); 3.98–4.60(m,5H); 3.22–3.48(m,2H); 2.50–2.91(m,4H); 1.60–2.18(m,6H).

EXAMPLE 42

2-[[2-(Hydroxymethyl)pyrrolidinyl]carbonyl]-N-phenylmethyl)-cyclopentanecarboxamide 2.80 g (8.5 mmol) of the title compound of Example 41 was dissolved in 150 ml of ethanol at 25° C. and 0.5 g (10%) palladium on carbon as a catalyst was added under a nitrogen atmosphere. The mixture was hydrogenated in a Parr apparatus at 25° C. under 50 psi hydrogen pressure for 12 hours, after which time thin layer chromatography analysis indicated complete conversion of starting material to product. The catalyst was removed by filtration and the filtrate evaporated in vacuo to afford the title compound in pure form as a colorless gum to a yield of 2.50 g (89%). TLC (90:10/$CH_2Cl_2$:MeOH): $R_f$=0.55.

EXAMPLE 43

2-[[2-(Formyl-1-pyrrolidinyl]carbonyl]-N-phenylmethyl)cyclopentanecarboxamide 2.50 g (7.6 mmol) of the title compound of Example 42 was reacted with 1.00 ml (11 mmol) of oxalyl chloride, 1.70 ml (22 mmol) of dimethyl sulfoxide, and 7.00 ml (50 mmol) of triethylamine in 40 ml of methylene chloride as described in Example 33. Work-up as described in Example 15 afforded the title compound in pure form as a gum without chromatographic purification. The yield was 2.30 g (93%). TLC (ethyl acetate): $R_f$=0.35. $^1$H NMR ($CDCl_3$) δ: 9.15–9.71(m,1H); 7.14–7.43(m,6H); 4.15–4.48(m,3H); 2.68– 3.85(m,6H); 1.52–2.30(m,8H). Low Resolution Mass Spectrum: m/e=329.2 (p+1). 2,4-DNP test: positive.

EXAMPLE 44

(S)-1-[2-(Phenylamino)benzoyl]-2-pyrrolidinemethanol 2.13 g (10 mmol) of N-phenylanthranilic acid, 1.35 g (10 mmol) of 1-hydroxybenzotriazole hydrate, 1.0 ml (10 mmol) of L-prolinol and 2.06 g (10 mmol) of DCC in 50 ml 1:1/methylene chloride:DMF. The coupling was carried out as described in Example 25 for the coupling of the acid and S(+)-2-pyrrolidinemethanol. Clean product of the title compound was obtained in virtually quantitative yield as a brownish gum without chromatographic purification. TLC (90:10/CH$_2$Cl$_2$:MeOH): R$_f$=0.75. $^1$H NMR (CDCl$_3$) δ: 7.50 (bs,1H); 6.75–7.36 (m,9H); 4.65–4.80(m,1H); 4.25–4.40 (m,1H); 3.38–3.85(m,4H); 1.55–2.15(m,4H).
We claim:
1. A compound of the formula:
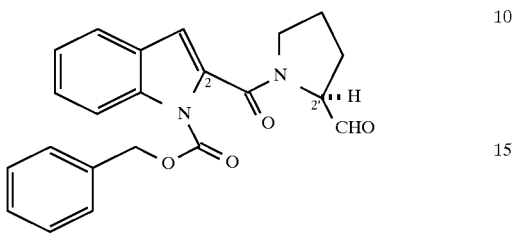
OR
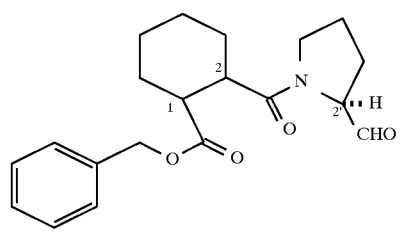
* * * * *